(12) United States Patent
Farah

(10) Patent No.: US 6,217,596 B1
(45) Date of Patent: Apr. 17, 2001

(54) CORNEAL SURFACE AND PUPILLARY CARDINAL AXES MARKER

(76) Inventor: Samir G. Farah, c/o Emile Jeha American University of Beirut, Beirut (LB)

( * ) Notice: Subject to any disclaimer, the term of this patent is extended or adjusted under 35 U.S.C. 154(b) by 0 days.

(21) Appl. No.: 09/388,076

(22) Filed: Sep. 1, 1999

(51) Int. Cl.[7] .................................................. A61F 9/00
(52) U.S. Cl. ........................................................... 606/166
(58) Field of Search .................................. 606/166, 167, 606/107; 604/19, 22, 27

(56) References Cited

U.S. PATENT DOCUMENTS

| | | | |
|---|---|---|---|
| 4,406,285 | * | 9/1983 | Villasenor et al. ................ 606/166 |
| 4,417,579 | * | 11/1983 | Soloviev et al. .................... 606/166 |
| 4,515,157 | * | 5/1985 | Fedorov et al. .................... 606/166 |
| 4,739,761 | * | 4/1988 | Grandon .............................. 606/166 |
| 5,314,439 | * | 5/1994 | Sugita ................................. 606/166 |
| 5,752,967 | * | 5/1998 | Kritzinger et al. ................. 606/166 |

* cited by examiner

Primary Examiner—Henry J. Recla
Assistant Examiner—(Jackie) Tan-Uyen T. Ho

(57) ABSTRACT

A corneal surface and pupillary cardinal axes marker instrument and a method of corneal marking are provided for purposes of astigmatic refractive surgery. The instrument comprises a head and a handle. The head features a blade and point marker assembly having readily visible ends as well as a blade assembly concept with a horizontally placed inclinometer allowing the exact determination and marking of the cardinal axes of the pupil, the marking of the surface of the corneal flap in LASIK surgery, and the measurement of positional eye cyclotorsion. The marking method involves preoperatively marking the corneal surface with suitable indicia in a pattern of radial lines extending over the inferior half of the cornea. The marking is done preoperatively while the patient is sitting at the slit lamp, with the inclinometer of the instrument horizontally leveled.

27 Claims, 1 Drawing Sheet

CORNEAL SURFACE AND PUPILLARY CARDINAL AXES MARKER

TECHNICAL FIELD

This invention relates to eye surgery and, more particularly, to cornea marker apparatus and means of marking for astigmatic corrective surgery such as astigmatic excimer laser surgery and astigmatic keratotomy.

CROSS REFERENCES TO RELATED APPLICATIONS

| 5,752,967 | May, 1998 | Kritzinger et al | 606/166 |
| 5,697,945 | December, 1997 | Kritzinger et al | 606/161 |
| 4,739,761 | April, 1988 | Grandon | 128/305 |

BACKGROUND OF THE INVENTION

Astigmatism is a refractive error along a specific meridian of the cornea; the image of an object falling in front or behind the retina in that meridian. Astigmatism has a power in diopters, and an axis denoting a direction on a 360-degree scale. The axis reflects the direction of the steepest or flattest meridian of the cornea.

Astigmatic surgery comprises flattening the steepest meridian or steepening the flattest meridian of the cornea. Using the excimer laser, the ablation profile is elliptical or butterfly-like according to the combination of the spherical and cylindrical refractive error. Several factors affect the optimal refractive outcome of astigmatic laser treatment. One of which is the exact alignment of the short axis of the elliptical ablation or of the butterfly-like ablation with the steepest meridian of the cornea in order to have the maximal corrective effect.

Astigmatism measurement is done while the patient is in a sitting position. However, astigmatism treatment is done while the patient is in a supine position. Several studies have detected ocular cyclotorsion, the eye turning around an axis passing through the center of the pupil, while the patient moves from the sitting to the supine position. If this eye movement is not taken into consideration when the patient lies under the laser, the direction of the short axis of the ellipse or of the butterfly-like ablation will not coincide with the steepest corneal meridian. Mathematically, missing the axis of astigmatism to be treated by 10 to 15 degrees leads to a treatment under-correction of 50%.

Currently, to detect any positional cyclotorsion of the eye, the refractive surgeons place a point mark at the 6 o'clock or the 3 and 9 o'clock axes of the pupil. This mark is put at the limbus of the eye, while the patient is sitting at the slit lamp. Under the laser, the alignment of the mark with either the 6 or 3 and 9 o'clock arms of a reticle incorporated in the visualization system of the laser is checked, while the reticle is kept centered on the pupil. If cyclotorsion occurs, the head of the patient is slightly rotated to align the laser reticle with the point mark in order to compensate for the eye movement.

The marking is done by free hand marking with a surgical ink pen after visually identifying the approximate limbal 6 o'clock position at the slit lamp. The prior art of free hand marking is unreliable, non-precise, and non-reproducible, with an error margin of 5 to 10 degrees leading to an estimated treatment under-correction between 18% and 35%.

Photorefractive keratectomy (PRK) and Laser in situ keratomileusis (LASIK) are the current laser refractive procedures. In PRK, the laser beam is applied to the corneal surface. While in LASIK a superficial round flap of the cornea is fashioned and lifted; then the laser beam is applied to the corneal bed beneath it. Subsequently the flap is flipped back to its original position, covering the treatment area. Using a marking dye, several radial marks are applied on the corneal surface before the flap is fashioned and lifted. These marks intersect the flap edges and ensure that the flap is repositioned to its original position by aligning them when the flap is flipped back at the end of the treatment. Traditionally, the marking of the corneal surface is done while the patient is lying under the laser. Furthermore, the marking of the corneal surface and the marking of the 6 o'clock position of the pupil are traditionally done in two separate procedures.

It is therefore an object of the present invention to provide improved cornea marker apparatus having marker blades that are conspicuous for purposes of radial placement to accurately determine and mark, on the cornea, the cardinal axes of the pupil (3, 6, and 9 o'clock axes) using a level.

It is another object of the invention to provide improved cornea marker apparatus having marker blades for radial placement to mark the surface of the corneal flap while the patient is sitting at the slit lamp.

It is still another object of the invention to provide an apparatus of the kind described having point markers to quantify the positional eye cyclotorsion.

It is yet another object to provide methods for marking the corneal surface while the patient is sitting at the slit lamp for purposes of corrective surgery.

BRIEF SUMMARY OF THE INVENTION

The invention is directed to an improvement in instrumentation and surgical technique. More particularly, the invention relates to an improved corneal surface marker and marking method for use during astigmatic corrective surgery. The advantage is accurately marking the cardinal axes of the pupil on the corneal surface and concomitantly marking the flap, in the case of LASIK, preoperatively while the patient is sitting at the slit lamp.

The corneal surface marker of the present invention comprises a marking component, preferably called head, and a handling component preferably called handle. On its marking side, the head comprises a number of radial marker blades, preferably five and a number of point markers, preferably six. Preferably, three of the radial blades mark the 3, 6, and 9 o'clock axes of the pupil, respectively and act also as cornea surface markers. The two other radial blades act as cornea surface markers. The marks are centered on the entrance pupil. The six point markers are used to measure the amount of positional cyclotorsion. The non-marking side of the head comprises a hair cross, a handle, and a horizontally placed inclinometer.

The most preferred method of marking the corneal surface according to the invention comprises placing the corneal surface marker over the area of the cornea to be marked while the patient is sitting at the slit lamp. The method is employed for preoperatively marking the corneal surface with suitable indicia in accordance with the radials and points of the marker. A reticle of a surgical laser instrument is aligned over the cardinal lines thereby permitting accurate astigmatic axis treatment.

These and other objects, features and advantages will be seen from the following description and accompanying drawings.

DETAILED DESCRIPTION OF THE PREFERRED EMBODIMENTS

1. The Marker

Figure 1:
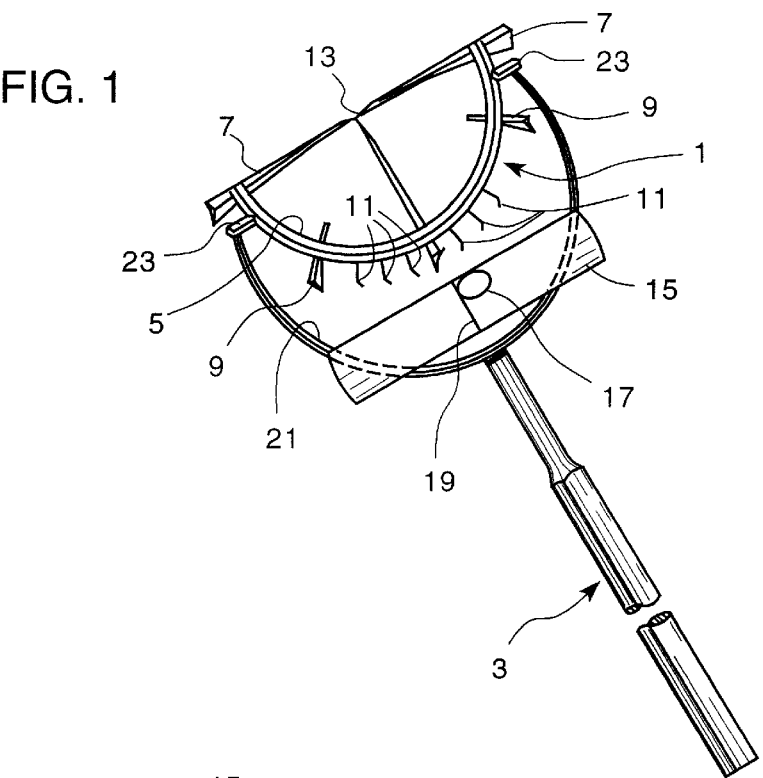
FIG. 1: Perspective and top view of a preferred cornea marker according to the invention.
Figure 2:
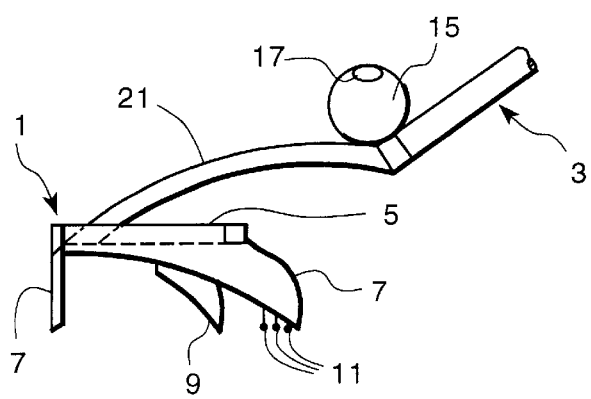
FIG. 2: Cross section view of a preferred cornea marker according to the invention.
Figure 3:
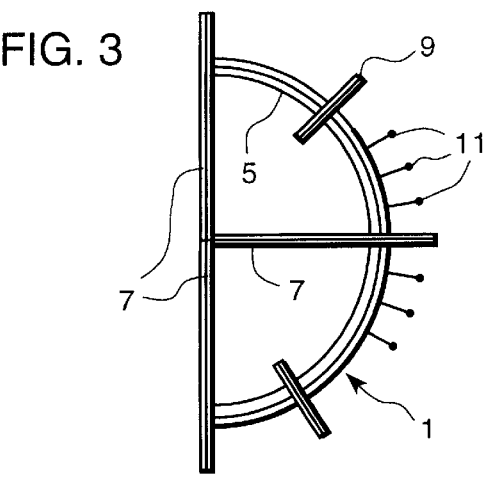
FIG. 3: Marking-side view of the head component of a preferred cornea marker according to the invention.

The corneal surface marker of the present invention comprises a combination of four concepts: radial linear markers for the 3,6,9 o'clock axes which will determine the cardinal axes of the pupil; radial linear markers for the corneal surface which will help in repositioning the flap in the case of LASIK; point markers which will quantify the amount of positional eye cyclotorsion, and a horizontally placed inclinometer which will determine the exact position of the cardinal axes of the pupil (FIG. 1).

The marker is made from any suitable material, such as preferably stainless steel or titanium. It may be disposable or resterilizable. The marker comprises a marking component preferably called head 1 and a handling component preferably called handle 3. The head 1 may be fixed to the handle 3 or detachable.

The marker head 1 is preferably semi-circular and includes a semi-circular support frame 5 of preferably 9 mm diameter which acts preferably as a fulcrum that attaches the different parts of the instrument. These parts include:

Three cardinal radial markers 7, each preferably 7 mm long, forming a T.

Two short radial markers 9 set so that the support frame 5 intersects them in the middle. The short radial markers 9 are set asymmetrically between the cardinal radial markers 7. The length of the short markers 9 is preferably 4 mm. The short marker 9 on the left is preferably at 45 degrees, the one on the right 9 is preferably at 60 degrees relative to the 6 o'clock cardinal radial marker 7.

Six point markers 11 are set at 10 degree intervals, symmetrically on both sides of the 6 o'clock cardinal marker 7, three on each side. The point markers 11 are attached to the support frame 5 in a manner that their marks fall on a circle of preferably 10 mm diameter.

The edges of the radial markers 7,9 have a similar concave curvature adapted in profile for co-extensive matching contact with the convex curvature of the outer corneal surface. The marks are preferably applied by painting the markers with any pharmacologically acceptably dye.

The T intersection forms a cross hair 13. The cross hair 13 is used to center the head of the instrument on the pupil. In a preferred description, the horizontal part of the cross hair 13 measures 3 mm and the vertical part 1.5 mm.

An inclinometer 15 made from any suitable material is incorporated horizontally onto the non-marking side of the instrument. The inclinometer 15 may be attached to the head or to the handle. It may be detachable or fixed. In a preferred description, the inclinometer 15 is fixed to the arms 21 of the handle 3. In the case of a glass inclinometer 15, it measures preferably 12 mm by 5 mm. The air bubble 17 in the inclinometer 15 gives the exact cardinal positions, when aligned with a mark 19. The mark 19 is preferably linear denoting the middle of the inclinometer 15. The inclinometer 15 may detect small tilts preferably of 0.5 degree or less. The handle 3 is attached to the marker head 1 preferably through the support frame 5. The handle 3 may be fixed to the frame 5 or detachable. In a preferred description, the handle 3 has two arms 21, each symmetrically attached to the support frame 5 with a pivot 23. The configuration allows the head 1 to pivot for co-extensive matching contact of its marking side with the convex curvature of the corneal surface.

2. Corneal Surface Marking Method

When the corneal marker described in detail above is used with a marking dye and properly placed in position over the corneal surface while the patient is sitting at the slit lamp thus allowing the laser instrumentation to be properly aligned with the astigmatic axis, the keratectomy and stromal reshaping by the surgeon may begin.

Specifically, the marking method comprises insuring that the slit lamp and the head of the patient are in a position perpendicular to the floor. The patient is then asked to look straight ahead as if looking through the surgeon. The slit light is made wide and dimmed. The lower lid is retracted. After painting the blades with a pharmacologically suitable dye, the marker is applied to the inferior half of the cornea while centering the cross hair on the pupillary center and making sure that the inclinometer is horizontally leveled. The lower lid is kept retracted for few seconds, preferably 10–15, allowing the time for the marks to dry. The patient is then positioned under the laser and asked to fixate at the fixation light. After inserting the lid speculum, the cardinal marks on the corneal surface and the laser reticle are checked for alignment, the reticle centering on the entrance pupil. In the case of LASIK, the alignment is checked again after lifting the flap, and before treatment.

CLAIMS

The invention has been described in terms of the preferred embodiments. The embodiments described above should not be viewed as limiting the scope of the invention. Modifications and ramifications may be made by those skilled in the art without departing from the spirit and scope of the invention. Thus, it is intended by the following claims to cover all such modifications and ramifications.

What is claimed is:

1. A surgical device for marking selected portions of a corneal surface of an eye having a pupil, comprising:
   a frame;
   a marker on the frame for marking the corneal surface;
   an inclinometer on the frame for indicating a vertical orientation of a cardinal axis of the pupil on the corneal surface.

2. The surgical device of claim 1 wherein the marker comprises at least one blade on the frame, the blade corresponding to a 6:00 cardinal axis of the pupil and wherein the inclinometer indicates the vertical orientation of the 6:00 cardinal axis.

3. The surgical device of claim 2 wherein the marker further comprises blades corresponding to 3:00 and 9:00 cardinal axes of the pupil.

4. The surgical device of claim 3 wherein the cardinal axes intersect at a center of a pupil of the eye.

5. The surgical device of claim 2 further comprising first and second asymmetric blades.

6. The surgical device of claim 5 wherein the first and second asymmetric blades are set asymmetrically between the cardinal axis blades.

7. The surgical device of claim 6 wherein the first asymmetric blade is preferably positioned at approximately positive 45 degrees with respect to the 6:00 cardinal axis, and wherein the second asymmetric blade is preferably positioned at approximately negative 60 degrees with respect to the 6:00 cardinal axis.

8. The surgical device of claim 1 further comprising a handle coupled to the frame.

9. The surgical device of claim 8 wherein the handle is snap-fit to the frame.

10. The surgical device of claim 8 wherein the inclinometer is fixed to the handle.

11. The surgical device of claim 8 wherein the inclinometer is removably coupled to the handle.

12. The surgical device of claim 1 further comprising point markers on the frame spatially positioned with respect to the cardinal axis.

13. The surgical device of claim 12 wherein the point markers are centered at a center of the pupil.

14. The surgical device of claim 12 wherein the point markers are used to measure positional cyclotorsion.

15. The surgical device of claim 14 wherein the point markers are positioned at preselected intervals with respect to the cardinal axis.

16. The surgical device of claim 15 wherein the intervals are approximately 10 degrees, and wherein the point markers are positioned along a semicircle having a radius of approximately 5 mm.

17. The surgical device of claim 1 wherein the inclinometer is fixed to the frame.

18. The surgical device of claim 1 wherein the inclinometer is removably coupled to the frame.

19. The surgical device of claim 1 wherein the inclinometer comprises a fluid-based inclinometer having a floating bubble for indicating the vertical orientation of the cardinal axis.

20. The surgical device of claim 19 wherein the inclinometer measures tilt with a precision less than or equal to 0.5 degree.

21. A method for marking selected portions of a corneal surface of an eye of a patient, the eye having a pupil, comprising:

providing a marker for marking a corneal surface;

leveling the marker using an inclinometer mounted to the marker for indicating a vertical orientation of a cardinal axis of the pupil; and marking said cardinal axis on the corneal surface.

22. The method of claim 21 further comprising positioning the patient in a seated position during marking of the corneal surface.

23. The method of claim 21 further comprising centering the marker on a pupil of the eye prior to marking the corneal surface.

24. The method of claim 21 further comprising aligning a reticle of a surgical laser relative to marks resulting from the marking.

25. The method of claim 21 further comprising removably coupling the inclinometer to the frame.

26. The method of claim 21 further comprising providing a handle coupled to the frame.

27. The method of claim 26 further comprising removably coupling the inclinometer to the handle.

\* \* \* \* \*